United States Patent [19]

Bauer et al.

[11] 4,120,852
[45] Oct. 17, 1978

[54] ORGANIC COMPOUNDS

[75] Inventors: Wilfried Bauer, Munchenstein; Janos Pless, Basel, both of Switzerland

[73] Assignee: Sandoz Ltd., Basel, Switzerland

[21] Appl. No.: 575,156

[22] Filed: May 7, 1975

[30] Foreign Application Priority Data

May 13, 1974 [CH] Switzerland ................. 6493/74
Oct. 4, 1974 [CH] Switzerland ................. 13377/74

[51] Int. Cl.² .................. C07C 103/52; A61K 37/00
[52] U.S. Cl. ....................... 260/112.5 S; 424/177
[58] Field of Search ............... 260/112.5 S; 424/177

[56] References Cited
U.S. PATENT DOCUMENTS 3,904,594  9/1975  Guillemin et al. ............ 260/112.5 S

*Primary Examiner*—Delbert R. Phillips
*Attorney, Agent, or Firm*—Gerald D. Sharkin; Robert S. Honor

[57] ABSTRACT

This invention provides new compounds of formula I,

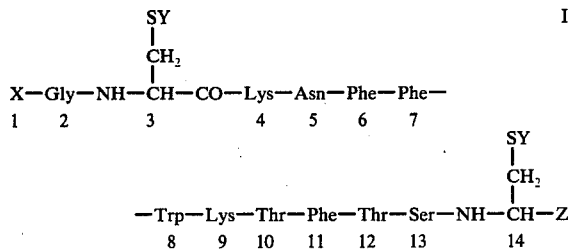

wherein
X is H-Ala, D-Ala, β-Ala, propionyl or Ac-Ala (wherein Ac is pharmaceutically acceptable acyl),
Y is hydrogen or a direct bond between the sulphur atoms in positions 3 and 14, and
Z is the radical —COOH, —COOR$_1$ (wherein R$_1$ is lower alkyl),

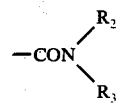

(wherein R$_2$ and R$_3$ independently are hydrogen or lower alkyl) or —CH$_2$OH,
with the proviso that X is other than H-Ala, when Z is COOH.

useful as agents for the treatment of Diabetes Mellitus, acromegaly and angiopathy.

16 Claims, No Drawings

ORGANIC COMPOUNDS

The present invention provides new peptides of formula I, $$\begin{array}{c}
\text{SY} \\
| \\
\text{CH}_2 \\
| \\
\text{X—Gly—NH—CH—CO—Lys—Asn—Phe—Phe—} \\
\text{1 \quad 2 \quad\quad\quad 3 \quad\quad\quad 4 \quad\;\; 5 \quad\;\; 6 \quad\;\; 7}
\end{array}$$

$$\begin{array}{c}
\text{SY} \\
| \\
\text{CH}_2 \\
| \\
\text{—Trp—Lys—Thr—Phe—Thr—Ser—NH—CH—Z} \\
\text{\;\;8 \quad\;\; 9 \quad\; 10 \quad\; 11 \quad\; 12 \quad\; 13 \quad\quad\quad\quad 14}
\end{array}$$

wherein

X is H-Ala, D-Ala, β-Ala, propionyl or Ac-Ala (wherein Ac is pharmaceutically acceptable acyl), Y is hydrogen or a direct bond between the sulphur atoms in positions 3 and 14, and Z is the radical —COOH, —COOR$_1$ (wherein R$_1$ is lower alkyl), $$-\text{CON}\begin{array}{c}R_2 \\ \diagdown \\ R_3\end{array}$$

(wherein R$_2$ and R$_3$ independently are hydrogen or lower alkyl) or —CH$_2$OH, with the proviso that X is other than H-Ala, when Z is COOH.

When Ac is acyl, this preferably is of 1 to 18 atoms, e.g. formyl, acetyl, benzoyl, palmitoyl. Conveniently pharmaceutically acceptable substituents may be present, e.g. halogen, as in trifluoroacetyl. When R$_1$, R$_2$ or R$_3$ is lower alkyl, this lower alkyl may contain 1 to 5, preferably 1 to 3 carbon atoms, and especially signifies methyl.

A peptide of formula I may be obtained by using as the last step methods which are conventional in the art of peptide synthesis.

The present invention accordingly provides a process for the production of a peptide of formula 1 which comprises (a) removing a least one protecting group present in a protected peptide of formula I,
   wherein X is hydrogen obtainable by joining together two peptide units by an amide linkage, the peptide units being such that when joined the correct amino acid sequence is obtained, or (b) oxidizing a peptide of formula I,
   wherein Y is hydrogen to produce a compound of formula I, wherein Y is a direct bond, or (c) aminating a peptide of formula I wherein Z is COOH or COOR, wherein R$_1$ is as defined above and Y is a direct bond, to produce a peptide of formula I wherein Z is $$-\text{CO—N}\begin{array}{c}R_2 \\ \diagdown \\ R_3\end{array}$$

wherein R$_2$ and R$_3$ are as defined above, and Y is a direct bond, or (d) selectively alkylating a peptide of formula I wherein Z is COOH and Y is a direct bond, to produce a peptide of formula I wherein Z is COOR$_1$ wherein R$_1$ is as defined above and Y is a direct bond.

Alternatively, the present invention provides a process for the production of a peptide of formula I as defined above in free form or having at least one protecting group thereon which comprises (a') joining together two peptide units, by an amide linkage, the peptide units being such that when joined the correct amino acid sequence is obtained, or (b') oxidizing a peptide of formula I,
   wherein Y is hydrogen to produce a compound of formula I, wherein Y is a direct bond Processes (a) and (a') may be carried out in conventional manner for joining amide linkages.

The most usual methods are the carbodiimide method, the azide method, the method of the activated esters and the anhydride method, as well as the Merrifield method.

The carboxyl group may, for example, be activated by conversion into an acid azide, anhydride, imidazolide, isoxazolide or an activated ester, or by reaction with a carbodiimide or N,N'-carbodiimidazole.

In one convenient method the thio moieties in positions 3 and 14 are protected, e.g. by p-methoxybenzyl. The lysine moiety in positions 4 and 10 may be protected, e.g. by carbobenzoxy. Any alanine moiety in position 1 may be protected, e.g. by carbobenzoxy.

The free functional groups which do not participate in the reaction may be protected during the build up of the peptides of the invention by the protective groups known in the synthesis of long chain peptides. A suitable radical for the blocking of the carboxyl group is the benzyl group, but other protective radicals, e.g. the methyl, ethyl, tert.amyl, amide or tert.butyl group, may likewise be used. A suitable radical for the blocking of an amino group, especially the ω-amino group of the lysine radical, is a carbobenzoxy group or a carbo-tert.butoxy group. The mercapto groups of the cystein radicals may, for example, be protected by acyl groups or preferably by arylmethyl groups or substituted arylmethyl groups, e.g. benzyl, p-methoxybenzyl, p-nitrobenzyl, diphenylmethyl or trityl.

These groups are especially suitable for use in the above-mentioned protected peptide of formula I.

Suitable reagents for the splitting off of groups protecting the thio moieties in positions 3 and 14 include hydrolyzing or reducing agents, such as hydrogen fluoride.

Processes (b) and (b') may be effected in conventional manner for forming S-S bridges in such peptides, e.g. using oxygen or preferably a ferricyanide conveniently potassium ferricyanide.

The groups Z may be interconverted, i.e. processes (c) and (d) using conventional synthetic methods, bearing in mind the other groups present.

The starting materials for the production of the peptides of the invention, insofar as they are unknown, may be obtained in accordance with known methods in peptide chemistry, whereby the amino acids may be joined together one at a time or after the formation of smaller peptidal units.

Free base forms of the peptides of formula I may be converted into acid addition salt forms in conventional manner and vice versa.

Suitable acid addition salts are those with organic acids, polymeric acids, and salts with inorganic acids. Acetic or hydrochloric acid is a suitable acid.

Free base forms may also be converted into complex form with inorganic anions, e.g. calcium, magnesium, manganese, aluminium, cobalt and zinc (especially halides, phosphates, pyrophosphates and polyphosphates) and/or e.g. polymeric organic substances such as polyoxygelatin, polyvinylpyrrolidone and carboxymethylcellulose, or sulphonic or phosphoric acid esters of alginic acid, dextran, polyphenols and polyalcohols, especially polyphloretine phosphate.

The following abbreviations are used:

| | | |
|---|---|---|
| Ala | = | L-alanyl |
| D—Ala | = | D-alanyl |
| β—Ala | = | β-alanyl |
| Gly | = | glycyl |
| Lys | = | L-lysyl |
| Asn | = | L-asparaginyl |
| Phe | = | L-phenylalanyl |
| Trp | = | L-tryptophanyl |
| Thr | = | L-threonyl |
| Ser | = | L-seryl |
| | | L-cysteinyl = L—NH—CH(CH$_2$SH)—CO— |
| BOC | = | tert. butyloxycarbonyl |
| Cbo | = | carbobenzoxy |
| MBzl | = | p-methylbenzyl |
| OMe | = | methoxy |
| OCP | = | 2,4,5-trichlorophenyloxy |
| ACOH | = | acetic acid |
| D—Cys | = | D-cysteinyl = D—NH—CH(CH$_2$SH)—CO— |
| Ac | = | acetyl |

In the following non-limitative Examples all temperatures are indicated in ° C.

When the title compounds are obtained, these are in acetate hydrate forms.

EXAMPLE 1

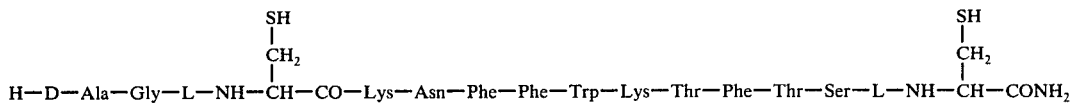

3.3 cc of anisole and 3.5 g of indole are added to 0.7 g of Cbo-D-Ala-Gly-Cys(MBzl)-Lys(Cbo)-Asn-Phe-Phe-Trp-Lys(Cbo)-Thr-Phe-Thr-Ser-Cys(MBzl)-NH$_2$. Approx. 40 cc of hydrogen fluoride are condensed with this mixture while cooling with dry ice, stirring is subsequently effected at 0° for 1 hour. The hydrogen fluoride is removed in a vacuum, the residue is stirred with 0.01 molar 2-mercapto-ethanol in ethyl acetate and filtration is effected. The residue is dissolved in a small amount of 5% acetic acid and the solution is purified by chromatography on Sephadex G 25 in a system of 0.01 molar 2-mercapto-ethanol in 5% acetic acid. The fractions containing the desired product are combined and lyophilized. The title compound is obtained. M.P. 210° (decomp.); $[α]_D^{20} = -40°$ in 1% acetic acid.

The Cbo-D-Ala-Gly-Cys-(MBzl)-Lys(Cbo)-Asn-Phe-Phe-Trp-Lys-(Cbo)-Thr-Phe-Thr-Ser-Cys(MBzl)-NH$_2$, used as starting material, is produced as follows:

(a) Cbo-Asn-Phe-Phe-OMe 85 g of Cbo-Phe-Phe-OMe are dissolved in 850 cc of hydrogen bromide/acetic acid 4 normal and the solution is concentrated to approx. ⅔ of its volume after one hour. Precipitation with ether and filtration with suction are effected. H-Phe-Phe-OMe.HBr is obtained. M.P. 196°; $[α]_D^{20} = +8.1$ in dimethyl sulphoxide.

40 g of H-Phe-Phe-OMe.HBr are dissolved in 400 cc of dimethyl formamide, and 44 g of Cbo-Asn-OCP and 16 cc of triethylamine are added. After standing at room temperature for 16 hours, the solution is concentrated by evaporation in a vacuum and the residue is boiled in isopropanol. After cooling, filtration with suction and washing with isopropanol and methanol are effected. Cbo-Asn-Phe-Phe-OMe is obtained. M.P. 226°; $[α]_D^{20} = -18.7°$ in dimethyl sulphoxide.

(b) BOC-Lys(Cbo)-Asn-Phe-Phe-OMe 77 g of Cbo-Asn-Phe-Phe-OMe are dissolved in 780 cc of hydrogen bromide/acetic acid 4 normal, and the solution is allowed to stand at room temperature for 1 hour. After concentrating, precipitation with 3 liters of ether and filtration with suction are effected. After drying, H-Asn-Phe-Phe-OMe.HBr is obtained. M.P. 195°; $[α]_D^{20} = +4°$ in dimethyl sulphoxide.

51 g of BOC-Lys(Cbo)-OH and 19 cc of triethylamine are dissolved in 500 cc of tetrahydrofuran, and 13 cc of chloroformic acid ethyl ester are added at −10°. After 5 minutes, a solution of 72 g of H-Asn-Phe-Phe-OMe.HBr and 23 cc of triethylamine in 800 cc of dimethyl formamide is added dropwise. After stirring at room temperature for 6 hours, the reaction mixture is concentrated by evaporation and chloroform is added. The precipitate is filtered off with suction, washed with chloroform and ethanol. BOC-Lys(Cbo)-Asn-Asn-Phe-OMe is obtained. M.P. 187°; $[α]_D^{20} = -22.4°$ in dimethyl sulphoxide.

(c) BOC-Cys(MBzl)-Lys(Cbo)-Asn-Phe-Phe-OMe 74 g of BOC-Lys(Cbo)-Asn-Phe-Phe-OMe are dissolved in 750 cc of trifluoroacetic acid/methylene chloride (9:1). After one hour, the solution is concentrated and precipitation is effected with ether. The precipitated material is filtered off with suction and washed with ether. H-Lys(Cbo)-Asn-Phe-Phe-OMe is obtained as trifluoroacetate. M.P. 216°; $[α]_D^{20} = -5.0°$ in dimethyl sulphoxide.

19 g of H-Lys(Cbo)-Asn-Phe-Phe-OMe trifluoroacetate and 15 g of BOC-Cys(MBzl)-OCP are dissolved in 150 cc of dimethyl formamide and 6.5 cc of triethylamine. After standing at room temperature for 16 hours, the reaction mixture is concentrated and precipitated with ether. The precipitated material is washed with ether, ethanol and acetone, and is dried. BOC-Cys(MBzl)-Lys-(Cbo)-Asn-Phe-Phe-OMe is obtained. M.P. 212°; $[α]_D^{20} = -20.7°$ in dimethyl sulphoxide.

(d) BOC-Gly-Cys(MBzl)-Lys(Cbo)-Asn-Phe-Phe-OMe 22 g of BOC-Cys(MBzl)-Lys(Cbo)-Asn-Phe-Phe-Ome are dissolved in 220 cc of trifluoroacetic acid/methylene chloride (9:1), and the solution is allowed to stand at room temperature for one hour. After concentrating, precipitation with ether and filtration with suction are effected. After drying, H-Cys(MBzl)-Lys-(Cbo)-Asn-Phe-Phe-OMe is obtained as trifluoroacetate. M.P. 195°; $[\alpha]_D^{20} = -6.2°$ in dimethyl sulphoxide.

4.5 g of BOC-Gly-OH and 3.6 cc of triethylamine are dissolved in 50 cc of tetrahydrofuran, and 2.5 cc of chloroformic acid ethyl ester are added at $-10°$. After 10 minutes, a solution of 24 g of H-Cys(MBzl)-Lys(-Cbo)-Asn-Phe-Phe-OMe trifluoroacetate and 6.0 cc of triethylamine in 250 cc of dimethyl formamide is added dropwise. After stirring at room temperature for 3 hours, the reaction mixture is concentrated by evaporation in a vacuum and the residue is washed several times with ether, ethanol and acetone. BOC-Gly-Cys(MBzl)-Lys(Cbo)-Asn-Phe-Phe-OMe is obtained. M.P. 111°; $[\alpha]_D^{20} = -17.0°$ in dimethyl sulphoxide.

(e) Cbo-D-Ala-Gly-Cys(MBzl)-Lys(Cbo)-Asn-Phe-Phe-OMe 4 g of BOC-Gly-Cys(MBzl)-Lys(Cbo)-Asn-Phe-Phe-OMe are dissolved in 40 cc of trifluoroacetic acid/methylene chloride (9:1) and the solution is allowed to stand at room temperature for ½ hour. Precipitation with ether and filtration with suction are effected, washing is effected with ether and H-Gly-Cys-(MBzl)-Lys-(Cbo)-Asn-Phe-Phe-OMe is obtained as trifluoroacetate. M.P. 194°; $[\alpha]_D^{20} = -14°$ in dimethyl sulphoxide.

900 mg of H-Gly-Cys(MBzl)-Lys(Cbo)-Asn-Phe-Phe-OMe trifluoroacetate, 440 mg of Cbo-D-Ala-OCP and 125 mg of 1-hydroxy-benzotriazole are dissolved in 10 cc of dimethyl formamide, 0.13 cc of triethylamine are added, and the mixture is stirred at room temperature for 20 hours. Precipitation with ether, filtration and successive washing with isopropanol, water, isopropanol and ether are effected, whereby the title compound is obtained. M.P. 220°; $[\alpha]_D^{20} = -17°$ in dimethyl sulphoxide.

(f) Cbo-D-Ala-Gly-Cys(MBzl)-Lys(Cbo)-Asn-Phe-Phe-NHNH$_2$ 0.8 g of Cbo-D-Ala-Gly-Cys(MBzl)-Lys(Cbo)-Asn-Phe-Phe-OMe are dissolved in 10 cc of dimethyl formamide, 1 cc of hydrazine hydrate is added, and the mixture is allowed to stand at room temperature for 20 hours. Precipitation with water and filtration are effected, and the residue is washed with water, then with methanol, and is dried, whereby the title compound is obtained. M.P. 235°; $[\alpha]_D^{20} = -28°$ in dimethyl sulphoxide.

(g) BOC-Lys(Cbo)-Thr-Phe-Thr-Ser-OMe 17 g of Cbo-Thr-Phe-Thr-Ser-OMe are dissolved in a mixture of methanol/dimethyl formamide, palladium charcoal is added and hydrogenation is effected at room temperature and normal pressure. The catalyst is filtered off and concentration is effected by evaporation in a vacuum. The resulting residue, 10.7 g of BOC-Lys(-Cbo)-OH and 4.2 g of hydroxy-benzotriazole, is dissolved in 80 cc of dimethyl formamide, the solution is cooled to $-5°$, and 3.2 cc of N-methylmorpholine and a solution of 6.1 g of dicyclohexylcarbodiimide in 30 cc of dimethyl formamide are added. Stirring is effected over night at room temperature, the precipitated dicyclohexyl urea is filtered off, and the filtrate is concentrated by evaporation. The residue is dissolved in ethyl acetate and washed with 5% sodium bicarbonate and water. The ethyl acetate phase is dried over sodium sulphate and subsequently concentrated. The precipitated product is filtered off and washed with ethyl acetate/ether. BOC-Lys(Cbo)-Thr-Phe-Thr-Ser-OMe is obtained. M.P. 130°; $[\alpha]_D^{20} = -7°$ in dimethyl formamide.

(h) BOC-Lys(Cbo)-Thr-Phe-Thr-Ser-NHNH$_2$ 7 g of BOC-Lys(Cbo)-Thr-Phe-Thr-Ser-OMe are dissolved in a mixture of dimethyl formamide and methanol, 8 cc of hydrazine hydrate are added, and the mixture is allowed to stand over night at room temperature. Water is added to the reaction mixture, this is stirred well, the precipitated product is filtered off, and the residue is washed with water and dried. BOC-Lys(-Cbo)-Thr-Phe-Thr-Ser-NHNH$_2$ is obtained. M.P. 198°; $[\alpha]_D^{20} = -5°$ in dimethyl formamide.

(i) BOC-Lys(Cbo)-Thr-Phe-Thr-Ser-Cys(MBzl)-OMe 4.15 g of BOC-Lys(Cbo)-Thr-Phe-Thr-Ser-NHNH$_2$ are dissolved in 40 cc of dimethyl formamide, the solution is cooled to $-20°$, 3 cc of 5 N hydrochloric acid in ether are added and then 0.58 cc of tert.-butyl nitrite are added, and the mixture is stirred at $-15°$ for 5 minutes. After the addition of 2.1 cc of triethylamine at $-20°$, the precipitated triethylamine hydrochloride is filtered off, and the filtrate is combined with a cold solution of 3.5 g of H-Cys(MBzl)-OMe CH$_3$SO$_3$H (M.P. 150°, $[\alpha]_D^{22} = -16°$ in dimethyl formamide, obtained from H-Cys(MBzl)-OH and methanesulphonic acid in methanol) and 1.3 cc of triethylamine in 20 cc of dimethyl formamide. The reaction mixture is allowed to stand at 0° over night, is subsequently concentrated in a vacuum, precipitation with ether, filtration and washing with ether, isopropanol and water are effected. Drying is effected, whereby the title compound is obtained. M.P. 186°; $[\alpha]_D^{22} = -15°$ in dimethyl formamide.

(j) BOC-Lys(Cbo)-Thr-Phe-Thr-Ser-Cys(MBzl)-NH$_2$ 2.5 g of BOC-Lys(Cbo)-Thr-Phe-Thr-Ser-Cys-(MBzl)-OMe are dissolved in a mixture of 30 cc of dimethyl formamide and 70 cc of methanol. The solution is saturated with ammonia gas at 0° and is allowed to stand at room temperature for 24 hours. Stirring is effected with ether, the precipitated product is filtered off, washing with ether and drying are effected, whereby the title compound is obtained. M.P. 205°; $[\alpha]_D^{20} = -15°$ in dimethyl formamide.

(k) BOC-Trp-Lys(Cbo)-Thr-Phe-Thr-Ser-Cys(MBzl)-NH$_2$ 1 g of BOC-Lys(Cbo)-Thr-Phe-Thr-Ser-Cys-(MBzl)-NH$_2$ is dissolved in 10 cc of a mixture of methylene chloride/trifluoroacetic acid (1:1), and the solution is allowed to stand at room temperature for 25 minutes. H-Lys(Cbo)-Thr-Phe-Thr-Ser-Cys(MBzl)-NH$_2$ trifluoroacetate is subsequently precipitated with ether, filtered off and washed out with ether. The residue is dissolved in 5 cc of dimethyl formamide, 0.73 g of BOC-Trp-OCP and 0.15 cc of triethylamine are added, and the mixture is allowed to stand at room temperature over night. Precipitation with ether/ethyl acetate (1:1), filtration and washing with ether are effected. The residue is recrystallized from methanol. After drying, the title compound is obtained. M.P. 212°; $[\alpha]_D^{20} = -17°$ in dimethyl formamide.

(1)
Cbo-D-Ala-Gly-Cys(MBzl)-Lys(Cbo)-Asn-Phe-Phe-Trp-Lys(Cbo)-Thr-Phe-Thr-Ser-Cys(MBzl)-NH$_2$ 0.65 g of BOC-Trp-Lys(Cbo)-Thr-Phe-Thr-Ser-Cys(MBzl)-NH$_2$ are dissolved in 6 cc of methylene chloride, and 0.54 cc of anisole, 0.59 g of indole and finally 6 cc of trifluoroacetic acid are added. The reaction mixture is allowed to stand at room temperature for 40 minutes and is subsequently precipitated with ether. After filtration, washing with ether and drying, H-Trp-Lys(Cbo)-Thr-Phe-Thr-Ser-Cys(MBzl)-NH$_2$ is obtained as trifluoroacetate.

0.59 g of Cbo-D-Ala-Gly-Cys(MBzl)-Lys(Cbo)-Asn-Phe-Phe-NHNH$_2$ are dissolved in 15 cc of dimethyl formamide, the solution is cooled to $-20°$, and 0.32 cc of 5.0 N hydrochloric acid in ether and then 0.60 cc of 10 % tert.butyl nitrite in dimethyl formamide are added, and the mixture is stirred at $-15°$ for 5 minutes. 0.35 cc of triethylamine are added, the precipitated triethylamine hydrochloride is filtered off, and the filtrate is combined with a cold solution of the H-Trp-Lys(Cbo)-Thr-Phe-Thr-Ser-Cys(MBzl)-NH$_2$ trifluoroacetate obtained above in 3 cc of dimethyl formamide. The mixture is allowed to stand over night at 0°, stirring is effected with 150 cc of methanol, filtration is effected, the residue is washed with methanol and ethyl acetate and with ether, and is dried, whereby the starting material is obtained. M.P. 230° (decomp.); $[\alpha]_D^{20} = -16°$ in dimethyl formamide.

EXAMPLE 2

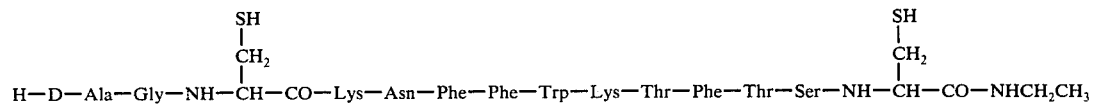

The title compound is produced in a manner analogous to that described in Example 1.

The Cbo-D-Ala-Gly-Cys(MBzl)-Lys(Cbo)-Asn-Phe-Phe-Trp-Lys(Cbo)-Thr-Phe-Thr-Ser-Cys(MBzl)-NH-CH$_2$CH$_3$, used as starting material, is produced as follows:

(a)
BOC-Lys(Cbo)-Thr-Phe-Thr-Ser-Cys(MBzl)-NH-CH$_2$-CH$_3$

A solution of 2 g of BOC-Lys(Cbo)-Thr-Phe-Thr-Ser-Cys(MBzl)-OMe in a mixture of dimethyl formamide/methanol is saturated with ethylamine gas while cooling and is allowed to stand at room temperature for 60 hours. The precipitated product is filtered off and washed with methanol. Drying is effected, whereby the title compound is obtained. M.P. 215°; $[\alpha]_D^{20} = -16°$ in dimethyl formamide.

(b)
BOC-Trp-Lys(Cbo)-Thr-Phe-Thr-Ser-Cys(MBzl)-NH-CH$_2$-CH$_3$

Production in a manner analogous to Example 1 (k). M.P. 224°; $[\alpha]_D^{20} = -19°$ in dimethyl formamide.

(c)
Cbo-D-Ala-Gly-Cys(MBzl)-Lys(Cbo)-Asn-Phe-Phe-Trp-Lys(Cbo)-Thr-Phe-Thr-Ser-Cys(MBzl)-NH-CH$_2$-CH$_3$

Production in a manner analogous to Example 1 (l). M.P. 240°; $[\alpha]_D^{20} = -17°$ in dimethyl formamide.

EXAMPLE 3

H—D—Ala—Gly—NH—CH(CH$_2$SH)—CO—Lys—Asn—Phe—Phe—Trp—Lys—Thr—Phe—Thr—Ser—NH—CH(CH$_2$SH)—CO—NHCH$_2$CH$_3$

The title compound is produced in a manner analogous to that described in Example 1.

The Cbo-D-Ala-Gly-Cys(MBzl)-Lys(Cbo)-Asn-Phe-Phe-Trp-Lys(Cbo)-Thr-Phe-Thr-Ser-Cys(MBzl)-N(CH$_2$CH$_3$)$_2$, used as starting material, is produced as follows:

(a)
BOC-Lys(Cbo)-Thr-Phe-Thr-Ser-Cys(MBzl)-N(CH$_2$CH$_3$)$_2$ 1.0 cc of diethylamine is added to a solution of 1 g of BOC-Lys(Cbo)-Thr-Phe-Thr-Ser-Cys(MBzl)-OMe in a mixture of dimethyl formamide/methanol, and the solution is allowed to stand at room temperature for 16 hours. Ether is added, the precipitated product is filtered off, washed with ether and dried, whereby the title compound is obtained. M.P. 188°; $[\alpha]_D^{20} = -14°$ in dimethyl formamide.

(b)
BOC-Trp-Lys(Cbo)-Thr-Phe-Thr-Ser-Cys(MBzl)-N(CH$_2$CH$_3$)$_2$

Production in a manner analogous to Example 1(k). M.P. 210°; $[\alpha]_D^{20} = -18°$ in dimethyl formamide.

(c)
Cbo-D-Ala-Gly-Cys(MBzl)-Lys(Cbo)-Asn-Phe-Phe-Trp-Lys(Cbo)-Thr-Phe-Thr-Ser-Cys(MBzl)-N(CH$_2$CH$_3$)$_2$

Production in a manner analogous to Example 1(l). M.P. 250°; $[\alpha]_D^{20} = -16°$ in dimethyl formamide.

EXAMPLE 4

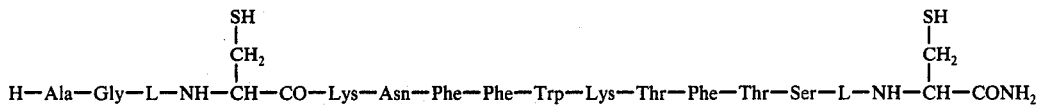

Cbo-Ala-Gly-Cys(MBzl)-Lys(Cbo)-Asn-Phe-Phe-OMe is built up in a manner analogous to that described in Example 1(e), whereby Cbo-Ala-OCP is used. M.P. 214°; $[\alpha]_D^{20} = -19°$ in dimethyl formamide.

Cbo-Ala-Gly-Cys(MBzl)-Lys(Cbo)-Asn-Phe-Phe-NHNH$_2$ is built up in a manner analogous to that described in Example 1(f). M.P. 245°; $[\alpha]_D^{20} = -22°$ in dimethyl formamide.

Cbo-Ala-Gly-Cys(MBzl)-Lys(Cbo)-Asn-Phe-Phe-Trp-Lys(Cbo)-Thr-Phe-Thr-Ser-Cys(Mbzl)-NH$_2$ is built up in a manner analogous to that described in Example 1(l). Treatment is subsequently effected with liquid hydrogen fluoride as indicated in Example 1. The title compound, having a M.P. of 218° (decomp.), is obtained; $[\alpha]_D^{20} = -36°$ in 1 % acetic acid.

filtered off and the filtrate is combined with a cold solution of 2.6 g of H-Cys(MBzl)-OBzl . methanesulphonate (M.P. 120°; $[\alpha]_D^{20} = -24°$ in dimethyl formamide, obtained from H-Cys(MBzl)-OH with benzyl alcohol and methanesulphonic acid) and 1.0 cc of triethylamine in 6 cc of dimethyl formamide. The reaction mixture is allowed to stand over night at 0°, is subsequently stirred together with 500 cc of ether, and the precipitated material is filtered off. The residue is dissolved in a mixture of methanol/dimethyl formamide, and water is subsequently added while stirring. The precipitated product is filtered off, washed with water and dried. BOC-Lys(Cbo)-Thr-Phe-Thr-Ser-Cys(MBzl)-OBzl is obtained. M.P. 169°; $[\alpha]_D^{20} = -16°$ in dimethyl formamide.

EXAMPLE 5

(b)

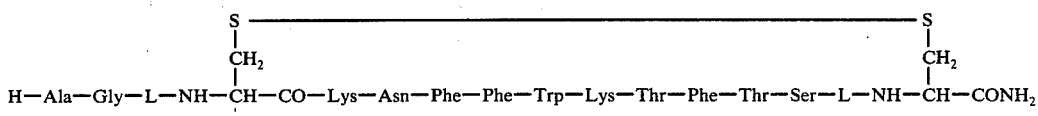

After oxidation of the title compound obtained in Example 4 with potassium ferricyanide and chromatography on Sephadex G-25, the title compound, is obtained;

EXAMPLE 6

BOC-Trp-Lys(Cbo)-Thr-Phe-Thr-Ser-Cys(MBzl)-OBzl 2.3 g of BOC-Lys(Cbo)-Thr-Phe-Thr-Ser-Cys(MBzl)-OBzl are dissolved in a mixture of 10 cc of methylene chloride and 6 cc of trifluoroacetic acid, and

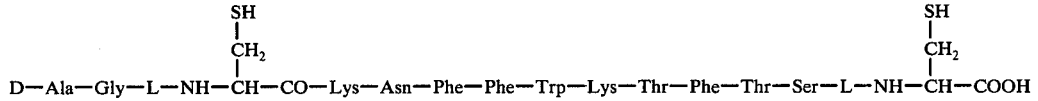

Cbo-D-Ala-Gly-Cys(MBzl)-Lys(Cbo)-Asn-Phe-Phe-Trp-Lys(Cbo)-Thr-Phe-Thr-Ser-Cys(MBzl)-OBzl is built up in a manner analogous to that described in Example 1 (a) to (l), whereby BOC-Trp-Lys(Cbo)-Thr-Phe-Thr-Ser-Cys(MBzl)-OBzl is used in intermediate step j) and treatment is subsequently effected as indicated in Example 1 with liquid hydrogen fluoride. The title compound, having a M.P. of 225° (decomp.), is obtained; $[\alpha]_D^{20} = -35°$ in 1 % acetic acid.

BOC-Trp-Lys(Cbo)-Thr-Phe-Thr-Ser-Cys(MBzl)-OBzl is produced as follows:

(a) BOC-Lys(Cbo)-Thr-Phe-Thr-Ser-Cys(MBzl)-OBzl the solution is allowed to stand at room temperature for 25 minutes. H-Lys(Cbo)-Thr-Phe-Thr-Ser-Cys(MBzl)-OBzl trifluoroacetate is subsequently precipitated with ether, filtered off and washed well with ether. The residue is dissolved in 7 cc of dimethyl formamide, 1.5 g of BOC-Trp-OCP and 0.3 cc of triethylamine are added, and the mixture is allowed to stand over night at room temperature. The product is precipitated with ether/ethyl acetate (1:1) and filtered. Drying is effected, whereby the starting material is obtained. M.P. 167°; $[\alpha]_D^{20} = -17.5°$ in dimethyl formamide.

EXAMPLE 7

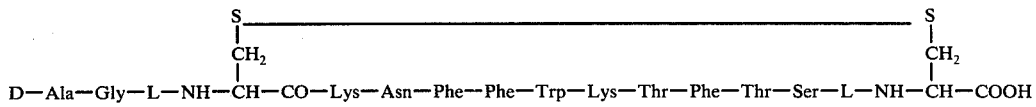

2.3 g of BOC-Lys(Cbo)-Thr-Phe-Thr-Ser-NHNH$_2$ are dissolved in 20 cc of dimethyl formamide, the solution is cooled to $-20°$, 1.8 cc of 5.5 N hydrochloric acid in ether are added and subsequently 0.33 cc of tert.butyl nitrite are added and the mixture is stirred at $-15°$ for 5 minutes. After the addition of 1.45 cc of triethylamine at $-20°$, the precipitated triethylamine hydrochloride is After oxidation of the title compound obtained in Example 6 with potassium ferricyanide, treatment with Bio-Rad AG 3X/4 and subsequent chromatography with Sephadex G-25 (dilute acetic acid), the title compound is obtained.

EXAMPLE 8

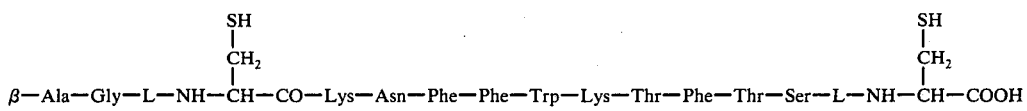

Cbo-β-Ala-Gly-Cys(MBzl)-Lys(Cbo)-Asn-Phe-Phe-Trp-Lys(Cbo)-Thr-Phe-Thr-Ser-Cys(MBzl)-OBzl is built up in a manner analogous to that described in Example 1 (a) to (l), whereby BOC-Trp-Lys(Cbo)-Thr-Phe-Thr-Ser-Cys(MBzl)-OBzl is used in intermediate step (j) and treatment is subsequently effected as indicated in Example 1 with liquid hydrogen fluoride. The title compound, having a M.P. of 229°–230° (decomp.), is obtained; $[\alpha]_D^{20} = -38°$ in 1 % acetic acid.

EXAMPLE 9

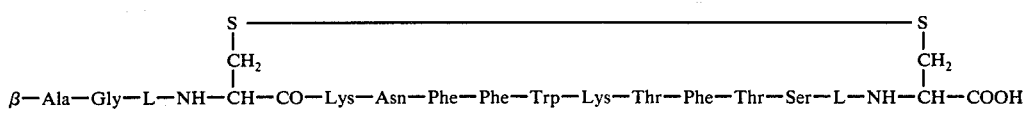

After oxidation of the title compound obtained in Example 8 with potassium ferricyanide and subsequent working up, the title compound, is obtained;

EXAMPLE 10

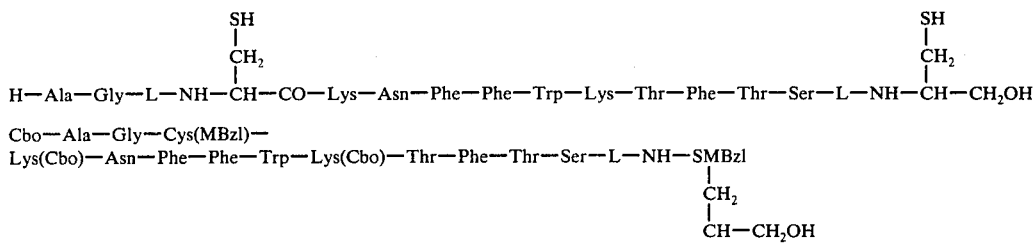

is built up in a manner analogous to that described in Example 1 (a) to (l), whereby

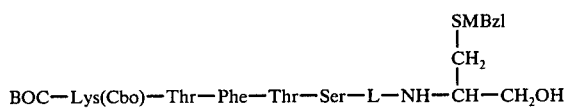

(M.P. 120°; $[\alpha]_D^{20} = -13°$ in dimethyl formamide) is used in intermediate step (j), obtained from BOC-Lys(-Cbo)-Thr-Phe-Thr-Ser-NHNH₂ and

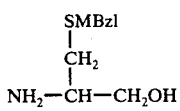

$[\alpha]_D^{20} = -21°$ in dimethyl formamide, obtained by treatment of H-Cys(MBzl)-OMe with NaBH₄). Treatment is subsequently effected with hydrogen fluoride as indicated in Example 1. The title compound is obtained.

EXAMPLE b 11

After oxidation of the title compound obtained in Example 10 with potassium ferricyanide and subsequent working up, the title compound is obtained.

EXAMPLE 12

100 to 2000 mg of H-D-Ala-Gly-Cys-Lys-Asn-Phe-Phe-Trp-Lys-Thr-Phe-Thr-Ser-Cys-OH are dissolved in 50 cc of water, 630 mg of zinc (II) chloride, 300 mg of phenol and 230 mg of sodium chloride are added, the pH of the solution is adjusted to 5 to 8 with a dilute caustic soda solution and distilled water is added to make up 100 cc.

EXAMPLE 13

The process is effected as described in Example 12, except that 460 mg of calcium chloride or 580 mg of manganese chloride or 440 mg of magnesium chloride are added in place of 630 mg of zinc (II) chloride.

EXAMPLE 14

The process is effected as described in Example 12, except that 200 mg of NaH₂PO₄ . H₂O are further added.

EXAMPLE 15

The process is effected as described in Example 12, except that 200 mg of NaH₂PO₄ . H₂O and 230 mg of carboxymethyl cellulose are further added.

EXAMPLE 16

The process is effected as described in Example 12, except that 200 to 5000 mg of polyphloretine phosphate are further added.

EXAMPLE 17

The process is effected as described in Example 12, except that 100 to 5000 mg of polyphloretine phosphate are added in place of zinc chloride.

EXAMPLE 18

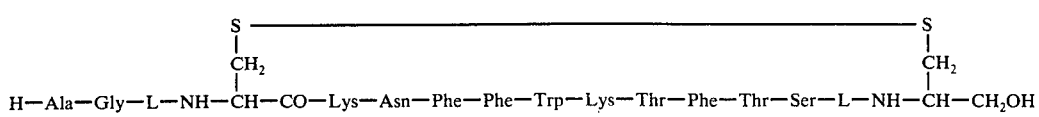

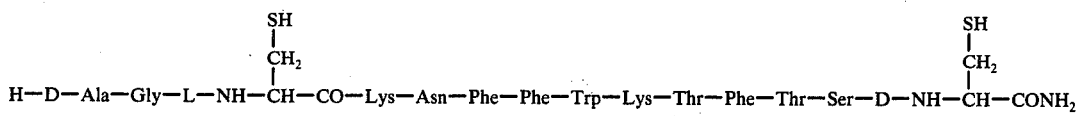

The title compound is produced in a manner analogous to that described in Example 1.

The Cbo-D-Ala-Gly-Cys(MBzl)-Lys(Cbo)-Asn-Phe-Phe-Trp-Lys(Cbo)-Thr-Phe-Thr-Ser-D-Cys(MBzl)-NH$_2$, used as starting material, is produced as follows:

(a) H-D-Cys(MBzl)-OH 15 g of D-cystine are dissolved in approximately 1.5 liters of dry ammonia, and sodium metal is added while stirring and boiling until the solution is blue coloured. Decolouration is effected with a small amount of ammonium chloride, and 30 g of p-methoxybenzyl chloride are added dropwise while stirring and boiling. The reaction mixture is evaporated to dryness, the residue is dissolved in water and extraction is effected with ethyl acetate. The pH of the aqueous phase is adjusted to the isoelectric point (pH 5–6) with hydrochloric acid. Filtration, washing with water and drying are effected, whereby H-D-Cys(MBzl)-OH is obtained. M.P. 204° (decomp.); $[\alpha]_D^{20} = -24°$ in 1N sodium hydroxide.

(b) BOC-D-Cys(MBzl)-OH 25 g of BOC azide are added to 24 g of H-D-Cys(MBzl)-OH in 200 cc of dioxane/water (1:1), and the mixture is stirred for 2 days at pH 10 (addition of caustic soda solution). Extraction is effected with ether, the aqueous phase is acidified with citric acid and the product is extracted with ethyl acetate. The ethyl acetate phase is washed with water, dried over sodium sulphate and concentrated. Crystallization is effected from ether/petroleum ether. M.P. 75°; $[\alpha]_D^{22} = +36°$ in dimethyl formamide.

(c) BOC-D-Cys(MBzl)-NH$_2$ 5 g of BOC-D-Cys(MBzl)-OH are dissolved in 60 cc of dry tetrahydrofuran, the solution is cooled to −15°, 1.85 cc of N-ethylmorpholine are added, and then 1.92 cc of chloroformic acid isobutyl ester are added, and the mixture is stirred for 10 minutes. Dry ammonia gas is subsequently passed through the solution at −15° while stirring, stirring is continued for 2 hours, whereby the temperature rises to room temperature. The reaction mixture is diluted with approximately 800 cc of ethyl acetate, is washed with water, and the organic phase is dried over sodium sulphate. Concentration, filtration, washing with ethyl acetate/ether and drying are effected, and the title compound is obtained. M.P. 140°; $[\alpha]_D^{20} = +26°$ in dimethyl formamide.

(d) H-D-Cys(MBzl)-NH$_2$ . trifluoroacetate 2.5 g of BOC-D-Cys(MBzl)-NH$_2$ are dissolved in 5 cc of methylene chloride, 6 cc of trifluoroacetic acid are added and the mixture is allowed to stand at room temperature for 45 minutes. The reaction mixture is stirred with ether, filtered, washed with ether and dried, whereby H-D-Cys(MBzl)-NH$_2$ . trifluoroacetate is obtained. M.P. 130°; $[\alpha]_D^{20} = -10°$ in dimethyl formamide.

(e) BOC-Lys(Cbo)-Thr-Phe-Thr-Ser-D-Cys(MBzl)-NH$_2$ 1.7 g of BOC-Lys(Cbo)-Thr-Phe-Thr-Ser-NHNH$_2$ are dissolved in 25 cc of dimethyl formamide, the solution is cooled to −20°, 1.6 cc of 5N hydrochloric acid in ether are added and then 0.24 cc of tert.butylnitrite are added, and the mixture is stirred at −15° for 5 minutes. After the addition of 1.2 cc of triethylamine at −20°, the precipitated triethylamine hydrochloride is filtered off and the filtrate (−20°) is combined with a cold solution of 0.8 g of H-D-Cys(MBzl)-NH$_2$ . trifluoroacetate in 3 cc of dimethyl formamide. 0.3 cc of triethylamine are added and the mixture is allowed to stand over night at 0°. The reaction mixture is concentrated in a vacuum, precipitated with ether and washed with methanol and water. Drying is effected, whereby the title compound is obtained. M.P. 190°; $[\alpha]_D^{20} = +6°$ in dimethyl formamide.

(f) BOC-Trp-Lys(Cbo)-Thr-Phe-Thr-Ser-D-Cys(MBzl)-NH$_2$

The title compound is produced in a manner analogous to that described in Example 1 k). M.P. 205°; $[\alpha]_D^{20} = +0.5°$ in dimethyl formamide.

(g) Cbo-D-Ala-Gly-Cys(MBzl)-Lys(Cbo)-Asn-Phe-Phe-Trp-Lys(Cbo)-Thr-Phe-Thr-Ser-D-Cys(MBzl)-NH$_2$

The title compound is built up in a manner analogous to that described in Example 1 (1), from BOC-Trp-Lys(Cbo)-Thr-Phe-Thr-Ser-D-Cys(MBzl)-NH$_2$ and Cbo-D-Ala-Gly-Cys(MBzl)-Lys(Cbo)-Asn-Phe-Phe-NHNH$_2$. M.P. 223° (decomp.); $[\alpha]_D^{20} = -4.3°$ in dimethyl formamide.

EXAMPLE 19

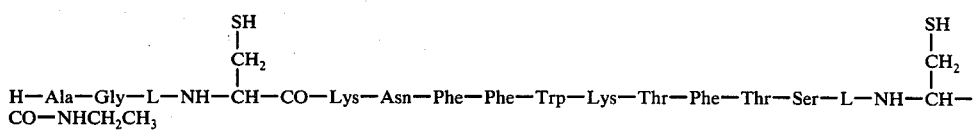

Cbo-Ala-Gly-Cys(MBzl)-Lys(Cbo)-Asn-Phe-Phe-Trp-Lys(Cbo)-Thr-Phe-Thr-Ser-Cys(MBzl)-NHCH$_2$CH$_3$ is built up in a manner analogous to that described in Example 2 (a) to (c). M.P. 230°; $[\alpha]_D^{20} = -15.5°$ in dimethyl formamide. Treatment is subsequently effected as indicated in Example 1 with liquid hydrogen fluoride. The title compound, having an M.P. of 220° (decomp.) is obtained; $[\alpha]_D^{20} = -42°$ in 1% acetic acid.

EXAMPLE 20

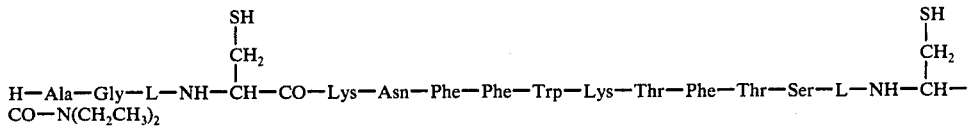

Cbo-Ala-Gly-Cys(MBzl)-Lys(Cbo)-Asn-Phe-Phe-Trp-Lys(Cbo)-Thr-Phe-Thr-Ser-Cys(MBzl)-N(CH$_2$CH$_3$)$_2$ is built up in a manner analogous to that described in Example 3 (a) to (c). M.P. 248° (decomp.); $[\alpha]_D^{20} = -17°$ in dimethyl formamide. Treatment is subsequently effected as indicated in Example 1 with liquid hydrogen fluoride. The title compound, having an M.P. of 205° (decomp.), is obtained; $[\alpha]_D^{20} = -35°$ in 1% acetic acid.

EXAMPLE 21

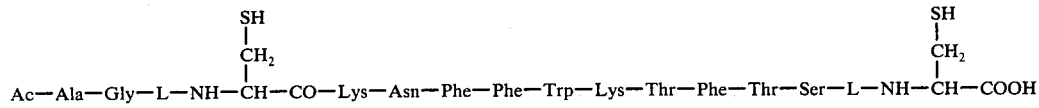

The title compound is produced in a manner analogous to that described in Example 1. M.P. 212° (decomp.); $[\alpha]_D^{20} = -25°$ in 1% acetic acid.

The Ac-Ala-Gly-Cys(MBzl)-Lys(Cbo)-Asn-Phe-Phe-Trp-Lys(Cbo)-Thr-Phe-Thr-Ser-Cys(MBzl)-Obzl, used as starting material, is produced as follows:

(a)
BOC-Ala-Gly-Cys(MBzl)-Lys(Cbo)-Asn-Phe-Phe-OMe 4 g of BOC-Gly-Cys(MBzl)-Lys(Cbo)-Asn-Phe-Phe-OMe are dissolved in 40 cc of trifluoroacetic acid/methylene chloride (9:1), and the solution is allowed to stand at room temperature for ½ hour. Precipitation with ether, filtering by suction and washing with ether are effected, whereby H-Gly-Cys(MBzl)-Lys(Cbo)-Asn-Phe-Phe-OMe is obtained as trifluoroacetate. M.P. 194°; $[\alpha]_D^{20} = -14°$ in dimethyl sulphoxide.

4.3 g of H-Gly-Cys(MBzl)-Lys(Cbo)-Asn-Phe-Phe-OMe trifluoroacetate, 1.7 g of BOC-Ala-OCP and 0.5 g of 1-hydroxybenzotriazol are dissolved in 60 cc of dimethyl formamide, 0.7 cc of triethylamine are added and the mixture is stirred at room temperature for 20 hours. Precipitation with ether, filtration and successive washing with isopropanol, water, isopropanol and ether are effected, whereby the title compound is obtained. M.P. 210°; $[\alpha]_D^{20} = -26°$ in dimethyl sulphoxide.

(b)
Ac-Ala-Gly-Cys(MBzl)-Lys(Cbo)-Asn-Phe-Phe-OMe 4.2 g of BOC-Ala-Gly-Cys(MBzl)-Lys(Cbo)-Asn-Phe-Phe-OMe are dissolved in 40 cc of trifluoroacetic acid/methylene chloride (9:1), and the solution is allowed to stand at room temperature for ½ hour. Precipitation with ether, filtration, washing with ether and drying are effected, whereby H-Ala-Gly-Cys(MBzl)-Lys(Cbo)-Asn-Phe-Phe-OMe is obtained as trifluoroacetate. M.P. 213° (decomp.); $[\alpha]_D^{20} = -16°$ in dimethyl formamide.

0.5 g of H-Ala-Gly-Cys(MBzl)-Lys(Cbo)-Asn-Phe-Phe-OMe trifluoroacetate are dissolved in 10 cc of dimethyl formamide, and 0.06 cc of acetyl chloride and 0.16 cc of triethylamine are added. The reaction mixture is allowed to stand at room temperature over night, is concentrated and is precipitated with ether. Filtration, washing with isopropanol and ether, and drying are effected, whereby the title compound is obtained. M.P. 207°; $[\alpha]_D^{20} = -27°$ in dimethyl formamide.

(c)
Ac-Ala-Gly-Cys(MBzl)-Lys(Cbo)-Asn-Phe-Phe-NHNH$_2$ 360 mg of Ac-Ala-Gly-Cys(MBzl)-Lys(Cbo)-Asn-Phe-Phe-OMe are dissolved in 10 cc of dimethyl formamide, 0.4 cc of hydrazine hydrate are added, and the mixture is allowed to stand at room temperature over night. Precipitation with water, filtration and washing with water, methanol and ether are effected. Drying is effected, whereby the title compound is obtained. M.P. 250° (decomp.); $[\alpha]_D^{20} = -36°$ in dimethyl formamide.

(d)
Ac-Ala-Gly-Cys(MBzl)-Lys(Cbo)-Asn-Phe-Phe-Trp-Lys(Cbo)-Thr-Phe-Thr-Ser-Cys(MBzl)-OBzl

The title compound is built up in a manner analogous to that described in Example 1 (1), from BOC-Trp-Lys(Cbo)-Thr-Phe-Thr-Ser-Cys(MBzl)-OBzl and Ac-Ala-Gly-Cys(MBzl)-Lys(Cbo)-Asn-Phe-Phe-NHNH$_2$. M.P. 228° (decomp.); $[\alpha]_D^{20} = -21°$ in dimethyl formamide.

EXAMPLE 22

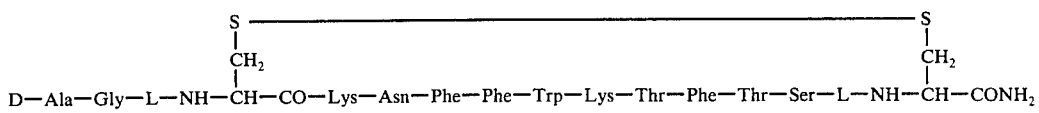

After oxidation of the title compound obtained in Example 1 with potassium ferricyanide, the title compound is obtained.

EXAMPLE 23

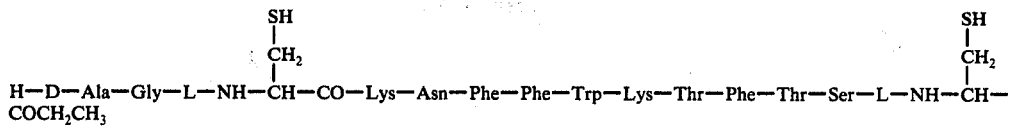

H—D—Ala—Gly—L—NH—CH—CO—Lys—Asn—Phe—Phe—Trp—Lys—Thr—Phe—Thr—Ser—L—NH—CH—
COCH$_2$CH$_3$

The title compound is produced in a manner analogous to that described in Example 1.

The peptides of formula I are useful as agents for the treatment of Diabetes Mellitus, acromegaly and angiopathy because of their growth hormone secretion inhibitory activity in standard animal tests, e.g. as follows:

Male rats anaesthetized with Nembutal are administered s.c. with the peptide. The rats are decapitated 15 minutes after administration, collecting the blood. The growth hormone concentration in the blood is determined in conventional manner by radio immunoassay.

The peptides are administered in this test s.c. at a dose of from about 0.5 to about 500 μg/kg animal body weight.

For the above mentioned use the dosage will, of course, vary depending on the compound employed, mode of administration and therapy desired. However, in general, satisfactory results are obtained when administered at a daily dosage of from 0.5 μg to about 1000 μg per kg animal body weight, conveniently given in divided doses 2 to 4 times a day or in sustained release form. For the larger mammal, the total daily dosage is in the range from about 0.07 to about 70 mg, and dosage forms suitable for parenteral administration comprise from about 0.02 mg to about 35 mg of the compounds admixed with a solid or liquid pharmaceutical carrier or diluent.

In the above test it is found that when the peptide is administered in complex form, e.g. with zinc or polyphloretine phosphate, a retard effect is observed.

For example 0.5 mg/kg animal body weight of a peptide is administered in a solution of from 0.1 to 100 mg/ml polyphloretinephosphate or from 0.1 to 10 mg/ml zinc chloride. It is therefore preferred to administer the peptide in the form of such complexes, e.g. substaneously or inframuscularly. Preferably these complexes are in solution from bufferred to a pH of between 5 and 8, e.g. with an alkali metal hydroxide or a phosphate buffer.

An indicated preparation contains 0.02 to 400 conveniently 0.2 to 200 parts of metal or organic polymer to every part of peptide present. In one embodiment a preparation contains from 2 mg to 80 mg of polyphloretic phosphate or the equivalent effective amount of another phosphate for every mg of peptide present or 1 mg of polyphloretic phosphate for every 0.02 to 20 mg of peptide present. In another embodiment a preparation contains from about 0.25 to about 0.5 mg of zinc cation or the equivalent effective amount of another metal for every mg of peptide present or 1 mmole of metal cation for every 20 to 500 mg of peptide present. Preferably 80 mg of polyphloretic phosphate is used for every mg of peptide present.

Alternatively the peptides of formula I may be administered in pharmaceutically acceptable acid addition salt form. Such acid addition salt forms exhibit the same order of activity as the free base forms and are readily prepared in conventional manner. The present invention also provides a pharmaceutical composition comprising a peptide of formula I in free form or in pharmaceutically acceptable acid addition salt or complex form in association with a pharmaceutical carrier or diluent.

The Example I compound exhibits especially interesting activity.

The above mentioned complexes may also be obtained according to the procedure described in application Ser. No. 562,949 filed Mar. 27, 1975, the contents of which are incorporated herein by reference, and using instead of the tetradecapeptide mentioned therein the peptide of formula I defined herein.

We claim:

1. A peptide of the formula

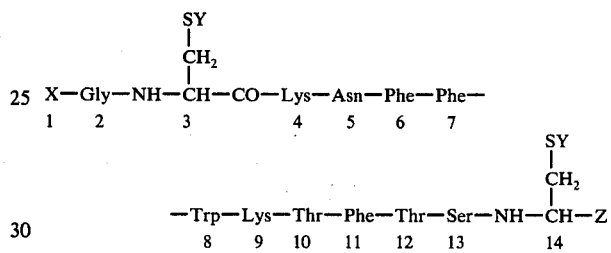

in free base form, pharmaceutically acceptable acid addition salt form or pharmaceutically acceptable complex form where X is H-Ala, D-Ala, β-Ala, propionyl or Ac-Ala (wherein Ac is pharmaceutically acceptable acyl), Y is hydrogen or a direct bond between the sulphur atoms in positions 3 and 14, and Z is the radical —COOH, —COOR$_1$ (wherein R$_1$ is lower alkyl),

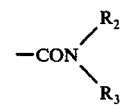

(wherein R$_2$ and R$_3$ independently are hydrogen or lower alkyl) or —CH$_2$OH, with the proviso that X is other than H-Ala, when Z is COOH.

2. A peptide of the formula

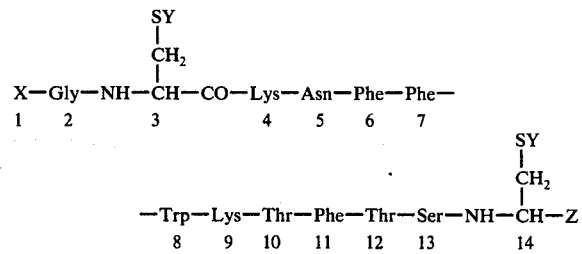

in free base form, pharmaceutically acceptable acid addition salt form or pharmaceutically acceptable complex form, where X and Y are as defined in claim 1, and Z represents

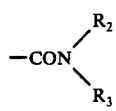

(wherein R₂ and R₃ independently are hydrogen or lower alkyl).

3. A peptide of the formula

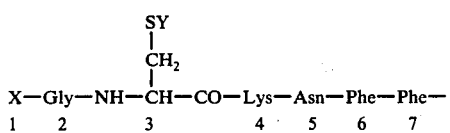

X and Y are as defined in claim 1, and Z represents

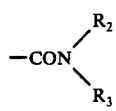

(wherein R₂ and R₃ are lower alkyl).

4. A peptide of claim 1, wherein the amino acid in positions 3 and 14 has the L-configuration.

5. A peptide of claim 1 wherein at least one of the amino acids in positions 3 and 14 has the D-configuration.

6. A peptide of claim 1 which is

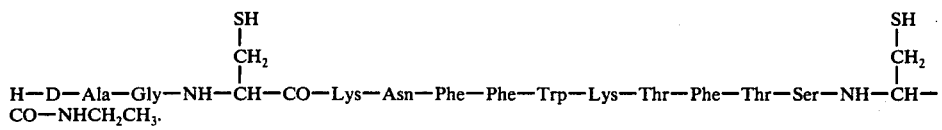

7. A peptide of claim 1 which is

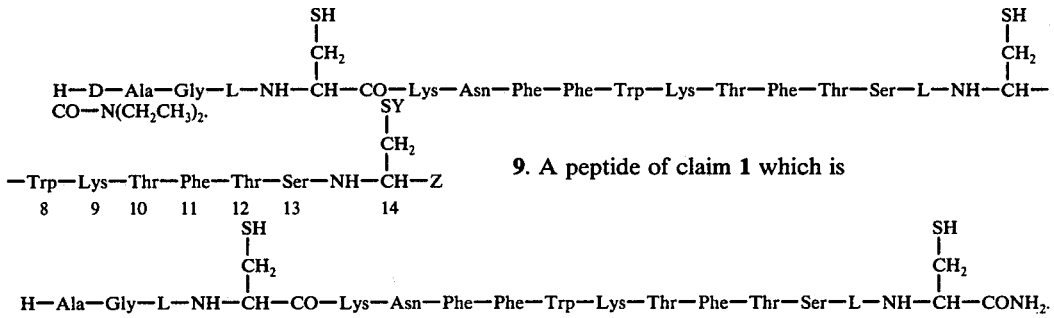

8. A peptide of claim 1 which is where

9. A peptide of claim 1 which is

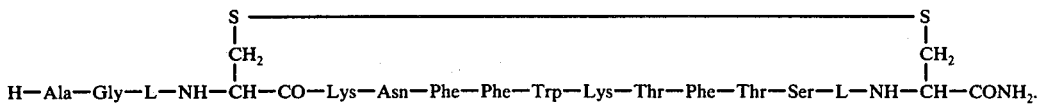

10. A peptide of claim 1 which is

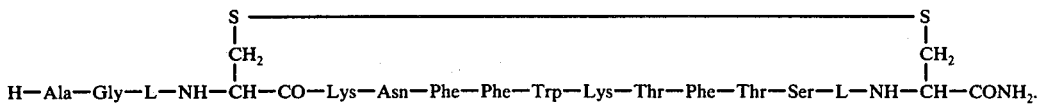

11. A peptide of claim 1 which is

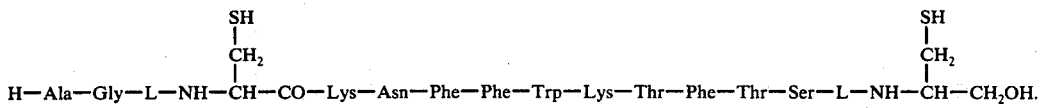

12. A peptide of claim 1 which is

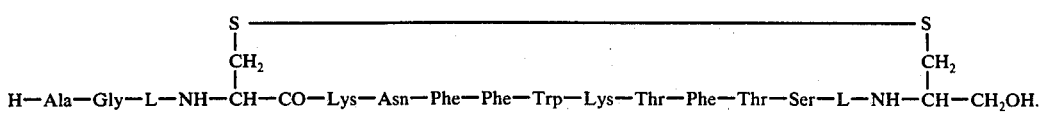

13. A peptide of claim 1 which is

14. A peptide of claim 1 which is
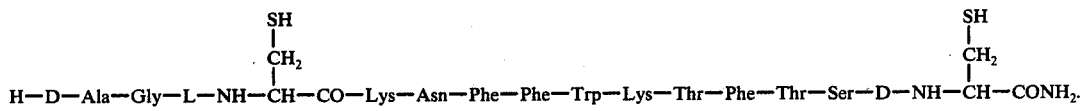
15. A peptide of claim 1 which is
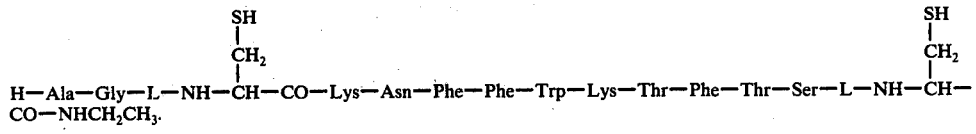
16. A peptide of claim 1 which is
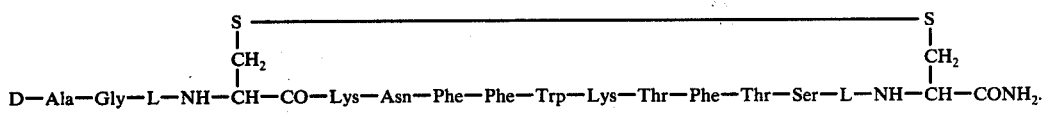
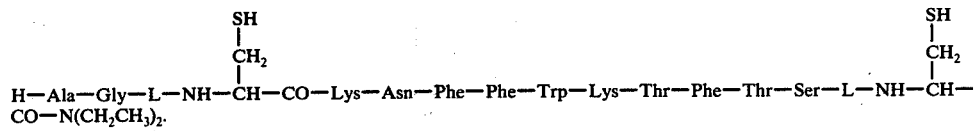
* * * * *